(12) United States Patent
Proksa

(10) Patent No.: US 9,055,919 B2
(45) Date of Patent: Jun. 16, 2015

(54) SPECTRAL IMAGING

(75) Inventor: Roland Proksa, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 880 days.

(21) Appl. No.: 13/000,384

(22) PCT Filed: Jun. 22, 2009

(86) PCT No.: PCT/IB2009/052672
§ 371 (c)(1),
(2), (4) Date: Dec. 21, 2010

(87) PCT Pub. No.: WO2010/007545
PCT Pub. Date: Jan. 21, 2010

(65) Prior Publication Data
US 2011/0097273 A1   Apr. 28, 2011

Related U.S. Application Data

(60) Provisional application No. 61/081,752, filed on Jul. 18, 2008.

(51) Int. Cl.
*A61B 6/03* (2006.01)
*A61B 6/00* (2006.01)
*A61B 5/00* (2006.01)
(Continued)

(52) U.S. Cl.
CPC .................. *A61B 6/504* (2013.01); *A61K 49/00* (2013.01); *A61B 5/4869* (2013.01); *A61B 6/032* (2013.01); *A61B 6/481* (2013.01); *A61B 6/482* (2013.01); *A61B 6/501* (2013.01); *A61M 5/007* (2013.01); *A61B 6/507* (2013.01)

(58) Field of Classification Search
CPC ......... A61B 6/03; A61B 6/481; A61M 5/007; A61K 49/00; A61P 43/00
USPC ................................... 600/425, 424
See application file for complete search history.

(56) References Cited

U.S. PATENT DOCUMENTS

| | | | | |
|---|---|---|---|---|
| 4,859,450 A | * | 8/1989 | Goldman | 424/9.34 |
| 6,645,147 B1 | * | 11/2003 | Jackson et al. | 600/458 |
| 6,745,066 B1 | * | 6/2004 | Lin et al. | 600/425 |

(Continued)

FOREIGN PATENT DOCUMENTS

| | | |
|---|---|---|
| WO | 2007034356 A2 | 3/2007 |
| WO | 2007039838 A2 | 4/2007 |

OTHER PUBLICATIONS

Suhonen, H., et al.; Simultaneous in vivo synchrotron radiation computed tomography of regional ventilation and blood volume in rabbit lung using combined K-edge and temporal subtraction; 2008; Physics in Medicine and Biology; 53(3)abstract.

(Continued)

*Primary Examiner* — Vani Gupta

(57) ABSTRACT

A method includes concurrently modulating administration of at least two different contrast agents to a subject during an imaging procedure based on a modulation profile. The at least two different contrast agents exhibit different spectral characteristics. The method further includes performing a spectral decomposition of data indicative of the at least two different contrast agents, determining concentrations of the at least two different contrast agents based on the spectral reconstruction, and determining a perfusion parameter based on a ratio of the concentrations and the modulation profile.

26 Claims, 3 Drawing Sheets

(51) Int. Cl.
*A61K 49/00* (2006.01)
*A61M 5/00* (2006.01)

(56) References Cited

U.S. PATENT DOCUMENTS

| | | | |
|---|---|---|---|
| 6,804,546 B1* | 10/2004 | Thompson et al. | 600/410 |
| 6,954,067 B2* | 10/2005 | Mistretta | 324/307 |
| 2003/0050555 A1* | 3/2003 | Critchlow et al. | 600/420 |
| 2003/0236458 A1* | 12/2003 | Hochman | 600/431 |
| 2004/0067300 A1* | 4/2004 | Edgren et al. | 427/2.14 |
| 2004/0101088 A1 | 5/2004 | Sabol et al. | |
| 2005/0107697 A1* | 5/2005 | Berke | 600/431 |
| 2005/0220265 A1* | 10/2005 | Besson | 378/16 |
| 2006/0036167 A1* | 2/2006 | Shina | 600/433 |
| 2007/0217570 A1* | 9/2007 | Grasruck et al. | 378/53 |
| 2007/0276194 A1* | 11/2007 | Netsch et al. | 600/300 |
| 2008/0137803 A1 | 6/2008 | Wu et al. | |
| 2008/0208068 A1* | 8/2008 | Robertson et al. | 600/508 |
| 2009/0052621 A1* | 2/2009 | Walter et al. | 378/53 |
| 2010/0113887 A1* | 5/2010 | Kalafut et al. | 600/300 |

OTHER PUBLICATIONS

Takai, M., et al.; Discrimination between thorotrast and iodine contrast medium by means of dual-energy CT scanning; 1984; Physics in Medicine and Biology; 29(8)abstract.

Schlomka, J. P., et al.; Experimental feasibility of multi-energy photon-counting K-edge imaging in pre-clinical computed tomography; 2008; Physics in Medicine and Biology; 53(15)4031-4047.

* cited by examiner

SPECTRAL IMAGING

CROSS REFERENCE TO RELATED APPLICATIONS

This application claims the benefit of U.S. provisional application Ser. No. 61/081,752 filed Jul. 18, 2008, which is incorporated herein by reference.

The following generally relates to spectral imaging, and finds particular application to computed tomography (CT). However, it also amenable to other medical imaging applications and to non-medical imaging applications.

A computed tomography (CT) scanner has been used to capture perfusion information, such as flow through vascular tissue, which can be used to facilitate diagnosing patients. For instance, a brain perfusion scan provides information that can be used to facilitate identifying mal-perfusion in stroke patients. In general, a conventional computed tomography perfusion (CTP) procedure includes intravenously administering a contrast agent bolus to a patient, which causes the x-ray density of the brain to temporarily increase as the contrast agent is taken up and flows through and washes out of the vascular structure of the brain, and performing a time series of CT scans of the patient's brain. The captured data can be used to trace the contrast agent as it flows through the brain and identify ischemic tissue and/or differentiate between irreversibly damaged or necrotic tissue (the core of the infarct) and potentially reversibly damaged or at-risk tissue (the penumbra of the infarct). The differences in the absorption in the time series provide relative measures of mean transition time (MTT), cerebral blood volume (CBV) and cerebral blood-flow (CBF).

Unfortunately, it may be difficult to measure the MTT value directly with a short and dense contrast bolus due to limitations of the injection rate. Often the MTT parameter is measured indirectly with a perfusion scan, a de-convolution technique to derive CBV and CBF, and the relation MTT=CBV/CBF. This may have limited reliability since the de-convolution process requires operator selection of a reference vessel for the input function, and the selection is prone to error. Furthermore, the accuracy of such a technique is limited since the pharmacokinetics is a complex function and the information carried by the CTP measurements are not well-suited for deriving the hemodynamic and perfusion parameters. Moreover, the contrast agent bolus is only temporarily present within the patient, and the time interval during which the contrast agent can be visualized is limited by the residence time of the contrast agent within the patient.

Another example perfusion procedure is a multi-phase liver study. For such a study, a contrast agent based CT procedure can be used to identify hyper and/or hypo perfused regions of the liver during the aortic (contrast uptake) phase, the portal venous (contrast wash out) phase, and/or the equilibrium (no contrast) phase. Unfortunately, such a study conventional requires administration of a contrast agent and then multiple scans (e.g., 3 to 5 scans) thereafter in order to capture the contrast agent in each of these phases as the contrast agent flows through the vessels. As such, patient dose may be high relative to protocols in which fewer scans are performed.

Aspects of the present application address the above-referenced matters and others.

According to one aspect, a method includes concurrently modulating administration of at least two different contrast agents to a subject during an imaging procedure based on a modulation profile. The at least two different contrast agents exhibit different spectral characteristics. The method further includes performing a spectral decomposition of data indicative of the at least two different contrast agents, determining concentrations of the at least two different contrast agents based on the spectral reconstruction, and determining a perfusion parameter based on a ratio of the concentrations and the modulation profile.

According to another aspect, a method administering at least first and second intravenous contrast agents, each with different spectral properties, to a subject, wherein the second intravenous contrast agent is administered after a first pre-set time delay from the administering of the first contrast agent. The method further includes performing a single spectral scan of the subject after a second pre-set time delay from the administering of the second contrast agent. The method further includes generating a first image of the first contrast agent representing a first physiological phase and a second image of the second contrast agent representing a second different physiological phase.

According to another aspect, a system includes a radiation source (110) that rotates about an examination region and emits polychromatic radiation that traverses the examination region and a detector array (118), located across from the radiation source (110) opposite the examination region, that detects radiation traversing the examination region and generates a signal indicative thereof. The system further includes an injector (114) that administers at least two different contrast agents for an imaging procedure based on a contrast agent modulation profile. The system further includes a reconstructor (120) that spectrally reconstructs the signal to generate a first image of the first contrast agent and a second image of the second contrast agent.

The invention may take form in various components and arrangements of components, and in various steps and arrangements of steps. The drawings are only for purposes of illustrating the preferred embodiments and are not to be construed as limiting the invention.

Figure 1:
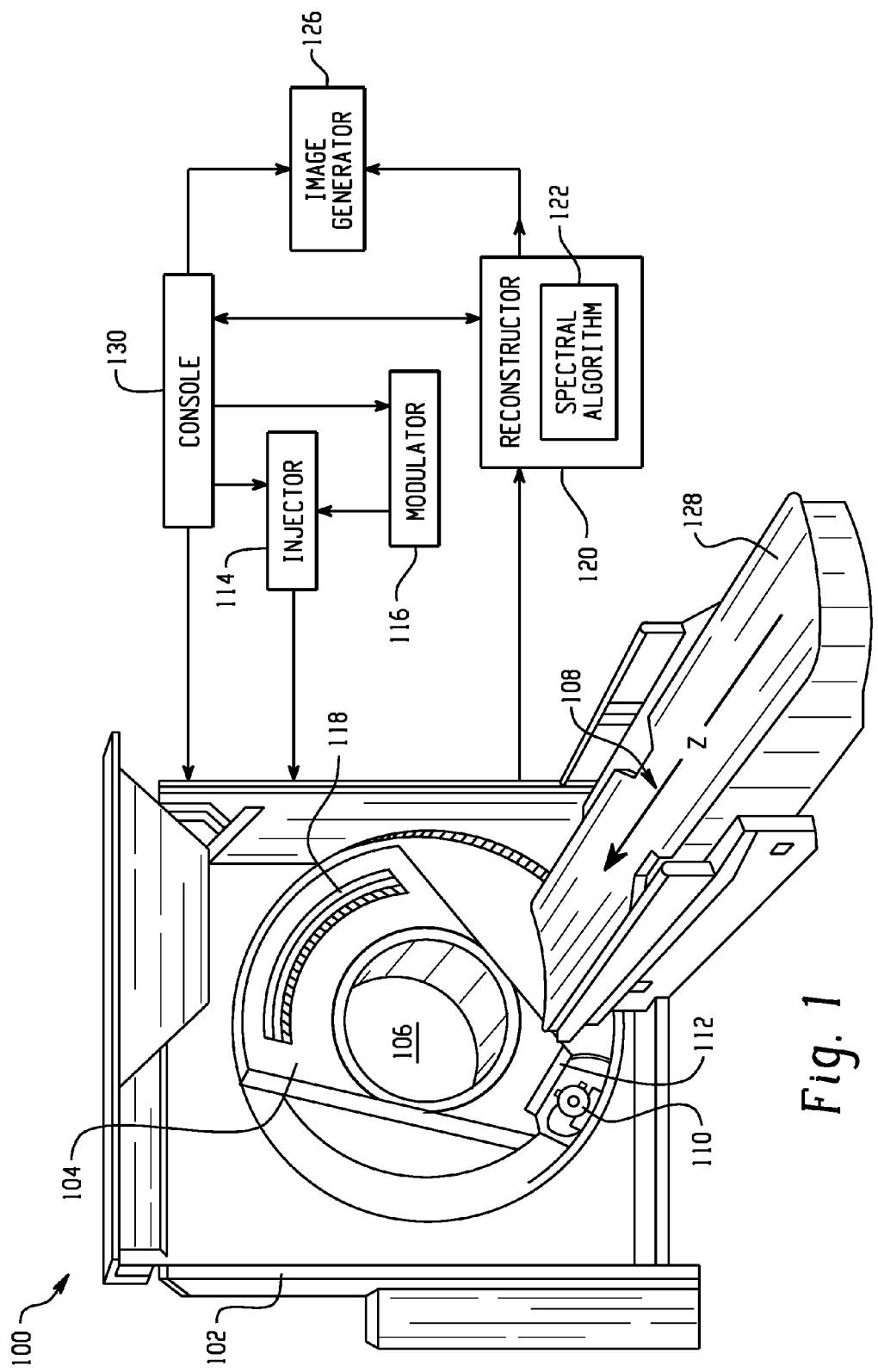
FIG. 1 illustrates an example imaging system.

FIG. 1 illustrates a computed tomography (CT) scanner 100 that includes a stationary gantry 102 and a rotating gantry 104, which is rotatably supported by the stationary gantry 102. The rotating gantry 104 rotates around an examination region 106 about a longitudinal or z-axis 108. A radiation source 110, such as an x-ray tube, is supported by and rotates with the rotating gantry 104 around the examination region 106 and emits polychromatic radiation. A collimator 112 collimates the emitted radiation to produce a generally fan, wedge, or cone shaped radiation beam that traverses the examination region 106. A radiation sensitive detector array 118 detects photons that traverse the examination region 106 and generates projection data indicative the examination region.

An injector 114 is configured to inject or administer a contrast medium in the patient for a scan. As described in greater detail below, in one instance the injector is used to concurrently administer at least two different contrast agents (e.g., a contrast agent containing gadolinium or iodine, etc.) with two different spectral properties in a same vessel or in different vessels. In another instance, the injector is used to successively administer two or more different contrast agents with a delay between the administering. A modulator 116 provides a control signal indicative of the injection pattern or profile of the two or more different contrast agents, including the concentrations of the two or more different contrast agents over time. The contrast agents can alternatively be manually administered by a clinician or the like.

A reconstructor 120 reconstructs the projection data and generates volumetric image data indicative thereof. In one instance, the reconstructor 120 employs a spectral algorithm 124 such as a K-edge algorithm. Such an algorithm allows for selective and quantitative imaging of materials with different spectral properties, such as one or more administered contrast agents. The reconstructor 120 may also employ conventional reconstruction algorithms, for example, a filtered backprojection algorithm or an iterative reconstruction algorithm.

An image generator 126 processes the volumetric image data and generates one or more images. In one instance, this includes generating at least a first image showing a first contrast agent and a second image showing a second contrast agent. If a tissue specific contrast agent(s) is used, the contrast is substantially absorbed by the tissue and the corresponding image(s) is indicative of the tissue. If a non-tissue specific contrast agent(s) is used, the corresponding image(s) is indicative of the vessels through which the contrast flows. One or more than one of the contrast agents can be specific or non-specific. The image generator 126 can also generate other images such as a conventional CT attenuation based image, another image showing another contrast agent, a Compton effect image, a photo-electric effect image, etc.

A patient support 128, such as a couch, supports the patient for the scan. A general purpose computing system 130 serves as an operator console. Software resident on the console 130 allows the operator to control the operation of the system 100 such as select imaging protocols including contrast agent based K-edge imaging protocols. As described in greater detail below, one such protocol includes concurrently modulating the administration of two or more different contrast agents during a scan to acquire information about organ perfusion, such as cerebral perfusion, with a time series of spectral CT scans. Another protocol includes successively administering different contrast agents, with a delay therebetween, and performing a scan to concurrently acquire information about different physiological phases in a single scan.

Figure 2:
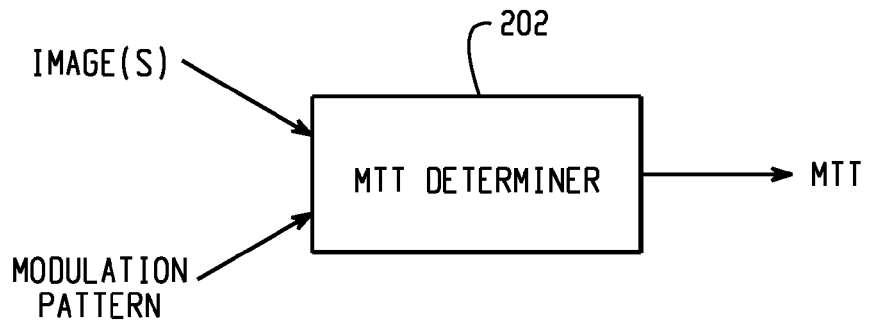
FIG. 2 illustrates an example MTT determiner.

In one embodiment, the scanner 100 is used to determine a perfusion parameter such as mean transit time (MTT). In one instance, this includes using a combination of concurrently modulating administration of contrast agents and a spectral scan, and determining the MTT based on the modulation technique, the contrast agents, and resulting image data. FIG. 2 illustrates an MTT determiner 202 that determines an MTT based on an image(s) generated from the image data and the contrast agent concentrations derived from the modulation pattern or profile.

Figure 3:
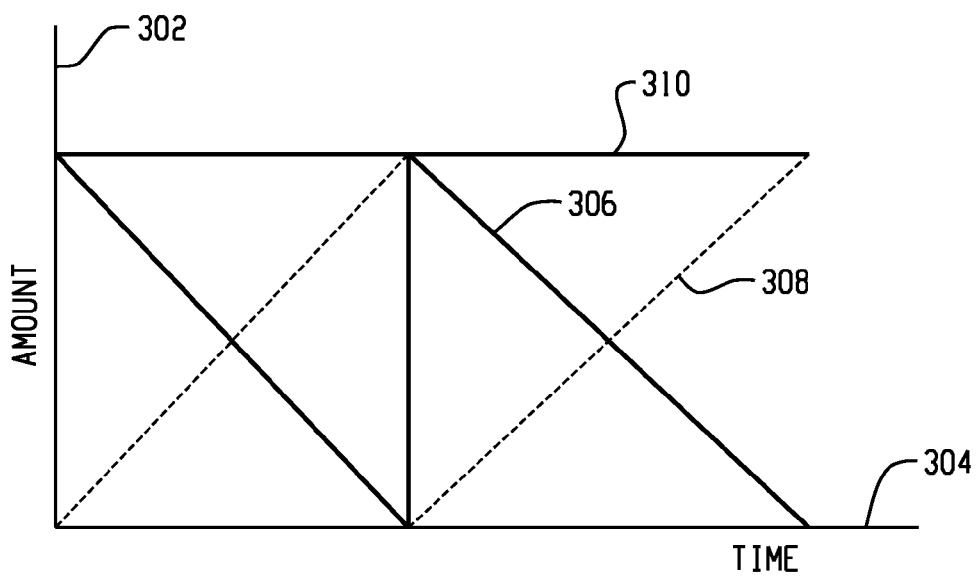
FIG. 3 illustrates example contrast agent modulation profiles.

Briefly turning to FIG. 3, example contrast agent modulation profiles are shown. In FIG. 3, the y-axis 302 represents the amount (e.g., milliliter per second (ml/sec), etc.) of the contrast agent administered and the x-axis 304 represents time. A first profile 306 shows an amount of a first contrast agent as a function of time, and a second profile 308 shows an amount of a second contrast agent as a function of time.

In this example, the profiles 306 and 308 are both saw tooth in shape. In other embodiments, the profiles can be different and/or otherwise shape, such as sinusoidal or triangular. Furthermore, the profiles 306 and 308 are inversions of each other. Moreover, in this example the aggregate amount of both contrast agents over time is substantially constant as shown at 310. In other embodiments, the aggregate amount of the contrast agents may change over time.

Returning to FIG. 2, a suitable example modulation profile or pattern of the contrast agents can be expressed in terms of two contrast agents as shown in modulation function 1:

$$\text{injection}(t) = \left[0.5 + \frac{F(\omega t)}{2}\right] fl_{CA_1} CA_1 + \left[0.5 - \frac{F(\omega t)}{2}\right] fl_{CA_2} CA_2,$$

Modulation Function 1 wherein injection(t) represents the total amount of the contrast agent injected over time, $F( )$ is the modulation function, $\omega$ represents the modulation frequency, $fl_{CA_1}$ represents the maximal flow rate of the first contrast agent, $fl_{CA_2}$ represents the maximal flow rate of the second contrast agent, $CA_1$ represents the measured concentration of the first contrast agent, and $CA_2$ represents the measured concentration of the second contrast agent.

Based on the modulation profile employed, for any image the measured ratio of the concentrations at any particular image point can be used to calculate an absolute transition time relative to the injection time. That is, a transition time can be determined by determining the time difference between the time when a particular ratio of the concentrations is administered and a point in an image where the ratio of the concentrations is about the same as the particular ratio of concentrations. For instance, the measured ratio at a particular image point or destination can be mapped to the modulation function shown in FIG. 3 to determine the corresponding start time of that concentration ratio, and the difference in time represents that transition time.

Figure 4:
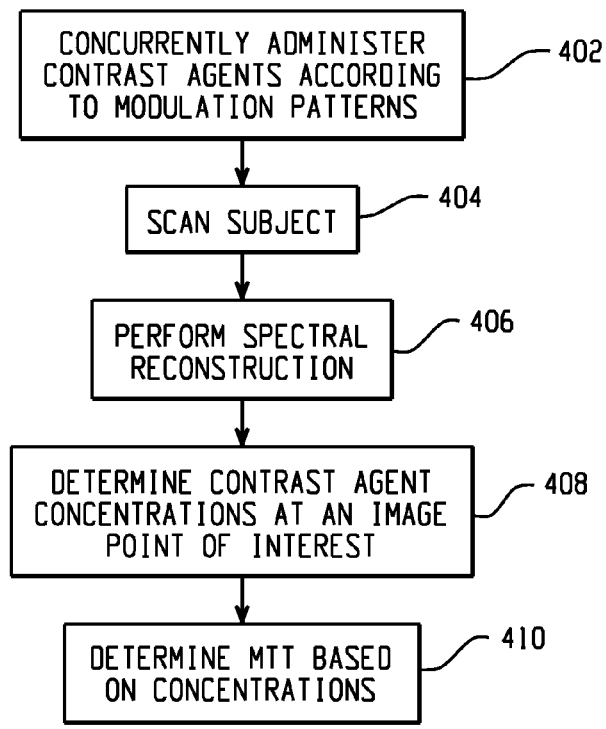
FIG. 4 illustrates an example method.

The above is illustrated in the method of FIG. 4. At 402, at least two different contrast agents having two different spectral properties are concurrently administered to a subject during an imaging procedure, using pre-determined contrast agent administration modulation patterns. At 404, the subject is scanned. At 406, a spectral reconstruction is performed on the resulting projection data, which is indicative of the at least two different contrast agents. At 408, the concentrations of the at least two different contrast agents are determined for a particular image point based on the spectral reconstruction. At 410, the MTT determiner determines an MTT for the particular image point based on a ratio of the concentrations and the contrast modulation patterns.

In another embodiment, the scanner 100 is used for multi-phase study such as a multi-phase liver study. Such studies can be used to identify hyper or hypo perfused regions (HCC or metastases) during the aortic phase, the portal venous phase and/or the equilibrium phase. As noted above, in a conventional study 3 to 5 scans may be performed after the contrast agent is injected in order to capture these phases. In this embodiment, the number of scans may be reduced via a suitable injection protocol combined with a spectral CT separation of the injected contrast agents.

Figure 5:
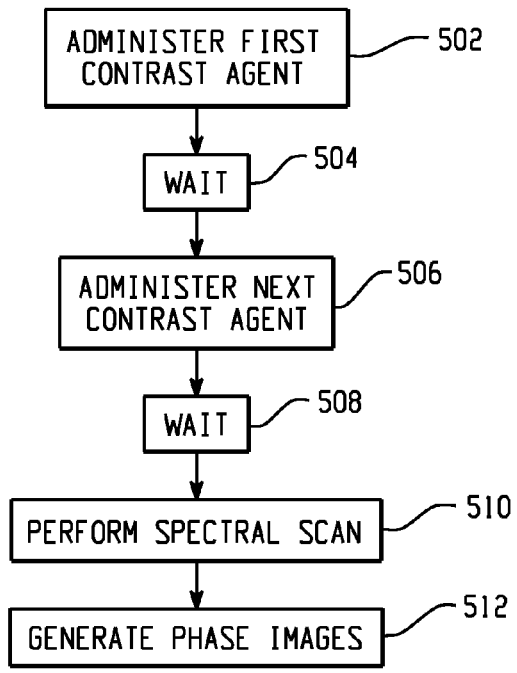
FIG. 5 illustrates an example method of a suitable injection protocol combined with a spectral CT separation of the injected contrast agents.

An example is provided in FIG. 5. At 502, a first contrast agent is administered for a first pre-set period of time. In one instance, the first pre-set period of time is ten (10) seconds. At 504, the next administration of a contrast agent is delayed by a second pre-set period of time. In one instance, the second pre-set period of time is ten (10) seconds. At 506, a second contrast agent is administered for a third pre-set period of time. In one instance, the third pre-set period of time is five (5) seconds. If another contrast agent is to be administered, it may also be delayed another pre-set time period. At 508, scanning is delayed by a fourth pre-set period of time. In one instance, the fourth pre-set period of time is ten (10) seconds.

At 510, a spectral CT scan is performed. Using the above protocol or other suitable protocol, during the scan the first contrast agent will be in the portal venous phase when the second contrast agent is in the aortic phase. The selective imaging capabilities of spectral CT allows the separation between the first and second contrast agents. At 512, two contrast images for two of the venous and the aortic are generated. As such, two contrast images for two of the phases can be captured in a single scan. When three or more contrast agents are administered, three or more images for the three phases are captured in a single scan.

In the above embodiments, two or more contrast agents are concurrently administered in the same vessel or successively administered in the same vessel. It is to be appreciated that administration of the contrast agents can alternatively be in different vessels. For example, the contrast agents can be administered at different injection points (left and right hemisphere, front and back lobe, etc.). Another application of this technique is to solve the inverse problem of a complex pharmacokinetic model. In other words, the free parameter of a pharmacokinetic model can be numerically determined with a proper multi contrast agent modulated injection protocol and selective imaging of the used contrast agents.

It is to be appreciated that other procedure and phases are also contemplated herein, including essentially any procedure involving tracking contrast flow through different phases is contemplated herein. For such procedure, a single scan can be performed to capture contrast in one or more of the different phases. Examples of other suitable phases include, but are not limited to, arterial, pancreatic, hepatic, liver, etc. phases.

As noted above, the reconstructor 120 can employ a K-edge algorithm. The following illustrates an example algorithm for two K-edge substances, such as the two contrast agents in the examples herein. Generally, the radiation source 110 emits polychromatic radiation with an emission spectrum T(E). The detection signal of the i-th detector channel is indicated by $d_i$ and can be described by Equation 1:

$$d_i = \int dE T(E) D_i(E) \exp(-(\rho_{photo} P(E) + \rho_{Compton} C(E) + \rho_{k\text{-}edge1} K_1(E) + \rho_{k\text{-}edge2} K_2(E)))$$ EQUATION 1 wherein $D_i(E)$ is the spectral sensitivity of the i-th detector channel, $\rho_{photo}$, $\rho_{compton}$, $\rho_{k\text{-}edge1}$ and $\rho_{k\text{-}edge2}$ are the density length products of the photo-electric effect, the Compton effect, the K-edge effect of the first substance and the K-edge effect of the second substance, respectively, and the energy dependent absorption spectra of the photo-electric effect, the Compton effect and the K-edge effect of the first substance and the K-edge effect of the second substance are indicated by $P(E)$, $C(E)$, $K_1(E)$ and $K_2(E)$, respectively. For N contrast materials, Equation 1 includes the following additional terms $\rho_{k\text{-}edge3} K_3(E) \ldots \rho_{k\text{-}edge(2+N)} K_{N+2}(E)$.

The input to the image generator 126 includes the energy-resolved detection signals $d_i$ for a plurality, e.g., four (4), energy bins. The emission spectrum T(E) and spectral sensitivity $D_i(E)$ generally are known. The absorption spectra $P(E)$, $C(E)$, $K_1(E)$ and $K_2(E)$ are known. Since the energy dependent functions and the detection signals $d_i$ are known and since at least four detection signals $d_1$-$d_4$ are available for at least four energy bins $b_1$-$b_4$, a system of at least four equations is formed having four unknowns which can thus be solved with known mathematical methods. If more than four energy bins are available, it is preferred to use a maximum likelihood approach that takes the noise statistics of the measurements into account.

The resulting density length products $\rho_{k\text{-}edge1}$ and $\rho_{k\text{-}edge2}$ are the first substance contribution and the second substance contribution, respectively, which can be used to generate a first K-edge image for the first substance and a second K-edge image for the second substance. In addition, the photo-electric density length product $\rho_{photo}$ can be used to reconstruct a photo-electric image, and the Compton effect density length product $\rho_{compton}$ can be used to reconstruct a Compton effect image. Generally, the Compton effect image and the photo-electric effect image show the object itself. These four images can be shown one by one, or they can be mixed, for example, a final image can show the first substance, the second substance and the Compton effect image and/or the photo-electric effect image. It is also possible to reconstruct one image showing one, some or all of the four components.

It is to be understood that the spectral decomposition can be performed on projection data or in the image domain.

Although the above is explained relative to particular applications, it is to be appreciated that the embodiments can be used to determine other parameters related to perfusion such, but not limited to, blood flow, blood volume, and/or other perfusion parameters.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

I claim:

1. A method, comprising:
performing a perfusion imaging procedure with a computed tomography scanner while concurrently modulating administration of at least two different contrast agents to a same vessel of a subject during the imaging procedure based on a modulation profile, wherein the at least two different contrast agents exhibit different spectral characteristics;
generating time series perfusion volumetric image data indicative of the at least two different contrast agents;
performing a spectral decomposition of the time series perfusion volumetric image;
determining concentrations of the at least two different contrast agents for an image of the time series perfusion volumetric image data based on the spectral decomposition;
determining a ratio of the concentrations;
mapping the ration of the concentrations to a time of the ratio in the modulation profile at which the at least two different contrast agents were administered with the ratio in the modulation profile; and
determining a perfusion parameter based on the mapping time between the ratio of the concentrations and the modulation profile.

2. The method of claim 1, wherein the modulation profile is one of triangular, saw tooth, or sinusoidal.

3. The method of claim 1, wherein a delivery rate of each contrast agent administered substantially continuously varies over time.

4. The method of claim 3, wherein an aggregate amount of the contrast agents is substantially constant over time.

5. The method of claim 1, wherein modulation profiles of the first and second contrast agents are inversely proportional.

6. The method of claim 1, wherein the spectral decomposition includes decomposing the time series volumetric image data into at least a first K-edge component for a first contrast agent and a second K-edge component for a second contrast agent.

7. The method of claim 1, further including concurrently administering at least one additional contrast agent with the at least two contrast agents, wherein the perfusion parameter is based on the concentrations of the three contrast agents and corresponding modulation profiles.

8. The method of claim 1, wherein the perfusion parameter is a transit time parameter, and further comprising:
determining the transition time parameter for the image as a difference between the mapped time and a start administration time of the at least two different contrast agents.

9. The method of claim 1, wherein the perfusion parameter is an absolute measure based on a time of injection.

10. The method of claim 1, wherein at least one of the at least first and second contrast agents is a tissue specific contrast agent.

11. The method of claim 1, wherein at least one of the at least first and second contrast agents is a non-specific contrast agent.

12. A method, comprising:
administering at least first and second contrast agents, each with different spectral properties, to a same vessel of a subject, wherein the second contrast agent is administered after a first pre-set time delay from the administering of the first contrast agent;
performing a single spectral scan of the subject with a computed tomography scanner after a second pre-set time delay from the administering of the second contrast agent; and
generating a first image of the first contrast agent representing a first physiological phase and a second image of the second contrast agent representing a second different physiological phase.

13. The method of claim 12, wherein the first phase is a portal venous phase and the second phase is an aortic phase.

14. The method of claim 12, wherein the first pre-set time is non-zero.

15. The method of claim 12, wherein the first pre-set time is about zero, and the at least first and second contrast agents are concurrently administered to different vessels.

16. The method of claim 12, further including decomposing data from the scan into at least a first K-edge component for the first contrast agent and a second K-edge component for the second contrast agent.

17. The method of claim 16, wherein the first K-edge component represents one of the physiological phases and the second K-edge component represents another of the physiological phases.

18. The method of claim 12, further including administering at least one additional contrast agent after a third preset delay from the administering of the second contrast agent, and performing the single spectral scan after a pre-set time delay from a last administered contrast agent.

19. The method of claim 18, further including generating a third image of the third contrast agent representing a third physiological phase, which is different from the first and second phases.

20. A system, comprising:
a radiation source that rotates about an examination region and emits polychromatic radiation that traverses the examination region;
a detector array, located across from the radiation source opposite the examination region, that detects radiation traversing the examination region and generates a signal indicative thereof;
an injector that administers at least two different contrast agents to a same vessel for an imaging procedure based on a contrast agent modulation profile;
a reconstructor that spectrally reconstructs the signal to generate time series perfusion volumetric image data indicative of the at least two different contrast agents; and
a perfusion parameter processor that determines concentrations of the at least two different contrast agents for a particular image point of the time series perfusion volumetric image data, determines a ratio of the concentrations, maps the ratio of the concentrations to a time of the ratio in the modulation profile at which the at least two different contrast agents were administered, and determines a transition time parameter for the image point as a difference between the mapped time and a start administration time of the at least two different contrast agents.

21. The system of claim 20, wherein the injector concurrently administers the first and second contrast agents based on different modulation patterns.

22. The system of claim 20, wherein the injector concurrently administers the first and second contrast agents in different vessels.

23. The system of claim 20, wherein the injector successively administers the first and second contrast agents with a time delay therebetween.

24. The system of claim 20, wherein the reconstructor decomposes the signal into components, including but not limited to, at least a first K-edge component and a second K-edge component, and further comprising:
an image generator that generates a first image ibased on the first K-edge component and a second image is based on the second K-edge component.

25. The system of claim 24, wherein the reconstructor further decomposes the signal into a Compton effect component and a photo-electric effect component, wherein the image generator generates a third image is based on the Component effect component and a fourth image is based on the photo-electric effect component.

26. The system of claim 20, further including a modulator that determines provides the modulation profile.

* * * * *